United States Patent [19]

Yamamoto et al.

[11] Patent Number: 5,627,065

[45] Date of Patent: May 6, 1997

[54] DNA FRAGMENT CONTAINING A GENE ENCODING CREATININE AMIDOHYDROLASE

[75] Inventors: Kazumi Yamamoto; Masanori Oka; Toshiro Kikuchi; Shigenori Emi, all of Tsuruga, Japan

[73] Assignee: Toyo Boseki Kabushiki Kaisha, Osaka, Japan

[21] Appl. No.: 908,620

[22] Filed: Jun. 29, 1992

Related U.S. Application Data

[63] Continuation of Ser. No. 538,274, Jun. 14, 1990, abandoned.

[30] Foreign Application Priority Data

Jun. 16, 1989 [JP] Japan ..................................... 1-152182

[51] Int. Cl.$^6$ ..................... C12N 9/80; C12N 15/55; C12N 15/70; C12N 15/74
[52] U.S. Cl. ..................... 435/228; 435/69.1; 435/252.3; 435/227; 435/320.1; 536/23.2; 935/14; 935/29; 935/72
[58] Field of Search .................... 435/227, 228, 435/320, 69.1, 172.3, 252.3, 252.33, 320.1; 536/23.2

[56] References Cited

U.S. PATENT DOCUMENTS

| | | | |
|---|---|---|---|
| 3,806,416 | 4/1974 | Mollering et al. | 435/288 |
| 3,806,420 | 4/1974 | Holz et al. | 435/231 |
| 3,907,644 | 9/1975 | Mollering et al. | 435/12 |
| 3,912,588 | 10/1975 | Mollering et al. | 435/136 |
| 4,652,639 | 3/1987 | Stabinsky | 435/91.52 |
| 4,861,717 | 8/1989 | Schumacher et al. | 435/172.3 |
| 5,043,279 | 8/1991 | Sagai et al. | 435/227 |

FOREIGN PATENT DOCUMENTS 0187138  7/1986  European Pat. Off. .

OTHER PUBLICATIONS

Tsuru, et al., 1976, Agricultural and Biological Chemistry 40:1011–1018 "Creatinine Decomposing Enzymes in *Pseudomonas* putida".

Shimizu, S., et al., 1986, Archives of Microbiology 145: 322–328, "Evaluation of two alternate metabolic pathways for creatinine degradation in microorganisms".

Donnelly, W. J., et al., 1977, International Journal of Biochemistry, 8: 11–16.

(List continued on next page.)

Primary Examiner—Robert A. Wax
Assistant Examiner—William W. Moore
Attorney, Agent, or Firm—Leydig, Voit & Mayer, Ltd.

[57] ABSTRACT

A DNA fragment that contains a gene encoding creatinine amidohydrolase is provided. This invention also provides a recombinant vector containing the said DNA fragment, a transformant containing the said vector, and a method for producing creatinine amidohydrolase by the use of the said transformant.

5 Claims, 6 Drawing Sheets

OTHER PUBLICATIONS

Suggs, S. V., et al., 1981, Proceedings, National Academy & Sciences, USA, 78(11), 6613–6617.

Latke, R., 1985, The Journal of Molecular Biology, 183: 1–12.

Short, J. M., et al., 1988, Nucleic Acids Research, 16(15): 7583–7600.

Ando, M., et al., 1977, Amino Acid—Nucleic Acid, 35:39–46.

Rikitake, K., et al., 1979, Journal of Biochemistry, 86(4): 1109–1117.

Shimizu, S., et al., 1986, Archives of Microbiology, 145:322–328.

Tsura, D., et al., 1976, Agricultural and Biological Chemistry, 40(5): 1011–1018.

Donnelly, W.J., et al., 1977, International Journal of Biochemistry 8(1): 11–16.

Suggs, S.V., et al., 1981, Proceedings of The National Academy of Sciences, U.S.A., 78(11): 6613–6617.

Latke, R., 1985, The Journal of Molecular Biology 183(1): 1–12.

Short, J.M., et al., 1988, Nucleic Acids Research, 16(15):7583–7600.

Fortkamp, E., et al., DNA, vol. 5, "Cloning and expression in *Escherichia coli* of a synthetic DNA for hirudin, the blood coagulation inhibitor in the leech", pp. 511–517 1986.

M. Ando et al. "Creatinine–decomposing enzymes in *Pseudomonas*. IV. Improvement of Culture Conditions for *Pseudomonas putida* C–83 and Induction of the Mutants of High Ability for Enzyme Production," Amino Acid—Nucleic Acid, vol. 35: 39–46, 1977.

K. Rikitake et al. "Creatinine Amidohydrolase (Creatininase) from *Pseudomonas putida*, Purification and Some Properties," J. Biochem., vol. 86: 1109–1117, 1979.

AMINO ACID SEQUENCE OF CREATININE AMIDOHYDROLASE

```
                                  10                                        20
Met Ser Lys Ser Val Phe Val Gly Glu Leu Thr Trp Lys Glu Tyr Glu Ala Arg Val Ala 30                                        40
Ala Gly Asp Cys Val Leu Met Leu Pro Val Gly Ala Leu Glu Gln His Gly His His Met 50                                        60
Cys Met Asn Val Asp Val Leu Leu Pro Thr Ala Val Cys Lys Arg Val Ala Glu Arg Ile 70                                        80
Gly Ala Leu Val Met Pro Gly Leu Gln Tyr Gly Tyr Lys Ser Gln Gln Lys Ser Gly Gly 90                                       100
Gly Asn His Phe Pro Gly Thr Thr Ser Leu Asp Gly Ala Thr Leu Thr Gly Thr Val Gln 110                                       120
Asp Ile Ile Arg Glu Leu Ala Arg His Gly Ala Arg Arg Leu Val Leu Met Asn Gly His 130                                       140
Tyr Glu Asn Ser Met Phe Ile Val Glu Gly Ile Asp Leu Ala Leu Arg Glu Leu Arg Tyr 150                                       160
Ala Gly Ile Gln Asp Phe Lys Val Val Val Leu Ser Tyr Trp Asp Phe Val Lys Asp Pro 170                                       180
Ala Val Ile Gln Gln Leu Tyr Pro Glu Gly Phe Leu Gly Trp Asp Ile Glu His Gly Gly 190                                       200
Val Phe Glu Thr Ser Leu Met Leu Ala Leu Tyr Pro Asp Leu Val Asp Leu Asp Arg Val 210                                       220
Val Asp His Pro Pro Ala Thr Phe Pro Pro Tyr Asp Val Phe Pro Val Asp Pro Ala Arg 230                                       240
Thr Pro Ala Pro Gly Thr Leu Ser Ser Ala Lys Thr Ala Ser Arg Glu Lys Gly Glu Leu 250                                       260
Ile Leu Glu Val Cys Val Gln Gly Ile Ala Asp Ala Ile Arg Glu Glu Phe Pro Pro Thr
```

FIG. 1

DNA SEQUENCE OF CREATININE AMIDOHYDROLASE

```
         10         20         30         40         50         60
ATGAGCAAGA GTGTTTTTGT AGGTGAGCTG ACCTGGAAGG AGTACGAGGC GCGTGTCGCG 70         80         90        100        110        120
GCAGGTGACT GCGTGCTCAT GCTGCCGGTC GGCGCCCTGG AACAGCACGG CCATCACATG 130        140        150        160        170        180
TGCATGAACG TCGATGTGCT GCTGCCCACG GCGGTGTGCA AGCGGGTCGC CGAGCGCATT 190        200        210        220        230        240
GGTGCGCTGG TCATGCCGGG GCTGCAGTAC GGCTACAAGT CCCAGCAGAA GTCCGGCGGC 250        260        270        280        290        300
GGCAATCACT TCCCCGGCAC CACCAGCCTG GATGGCGCCA CCCTGACTGG CACGGTGCAG 310        320        330        340        350        360
GACATCATCC GCGAGCTGGC GCGCCATGGT GCGCGTCGCC TGGTACTGAT GAACGGCCAC 370        380        390        400        410        420
TACGAAAATT CCATGTTCAT CGTCGAAGGC ATCGACCTCG CCCTGCGCGA GCTGCGCTAT 430        440        450        460        470        480
GCCGGCATCC AGGACTTCAA AGTGGTGGTG CTCTCCTACT GGGACTTCGT CAAGGACCCG 490        500        510        520        530        540
GCTGTGATCC AGCAGCTCTA TCCCGAGGGC TTCCTCGGCT GGGACATCGA GCACGGCGGC 550        560        570        580        590        600
GTCTCCGAGA CCTCCCTGAT GCTGGCTTTG TACCCGGACC TGGTGGACCT GGACCGCGTC 610        620        630        640        650        660
GTCGATCACC CACCTGCAAC CTTCCCACCC TATGACGTGT TTCCGGTCGA CCCGGCCCGT 670        680        690        700        710        720
ACGCCGGCGC CGGGCACTCT GTCGTCGGCG AAGACGGCCA GCCGAGAGAA GGGCGAGTTG 730        740        750        760        770        780
ATCCTGGAGG TCTGCGTCCA GGGCATTGCC GACGCTATCC GCGAGGAGTT CCCGCCCACC

TGA
```

FIG. 2

DNA SEQUENCE AND AMINO ACID SEQUENCE
OF CREATININE AMIDOHYDROLASE

```
                                            30                                              60
ATG AGC AAG AGT GTT TTT GTA GGT GAG CTG ACC TGG AAG GAG TAC GAG GCG CGT GTC GCG
Met Ser Lys Ser Val Phe Val Gly Glu Leu Thr Trp Lys Glu Tyr Glu Ala Arg Val Ala 90                                             120
GCA GGT GAC TGC GTG CTC ATG CTG CCG GTC GGC GCC CTG GAA CAG CAC GGC CAT CAC ATG
Ala Gly Asp Cys Val Leu Met Leu Pro Val Gly Ala Leu Glu Gln His Gly His His Met 150                                             180
TGC ATG AAC GTC GAT GTG CTG CTG CCC ACG GCG GTG TGC AAG CGG GTC GCC GAG CGC ATT
Cys Met Asn Val Asp Val Leu Leu Pro Thr Ala Val Cys Lys Arg Val Ala Glu Arg Ile 210                                             240
GGT GCG CTG GTC ATG CCG GGG CTG CAG TAC GGC TAC AAG TCC CAG CAG AAG TCC GGC GGC
Gly Ala Leu Val Met Pro Gly Leu Gln Tyr Gly Tyr Lys Ser Gln Gln Lys Ser Gly Gly 270                                             300
GGC AAT CAC TTC CCC GGC ACC ACC AGC CTG GAT GGC GCC ACC CTG ACT GGC ACG GTG CAG
Gly Asn His Phe Pro Gly Thr Thr Ser Leu Asp Gly Ala Thr Leu Thr Gly Thr Val Gln 330                                             360
GAC ATC ATC CGC GAG CTG GCG CGC CAT GGT GCG CGT CGC CTG GTA CTG ATG AAC GGC CAC
Asp Ile Ile Arg Glu Leu Ala Arg His Gly Ala Arg Arg Leu Val Leu Met Asn Gly His 390                                             420
TAC GAA AAT TCC ATG TTC ATC GTC GAA GGC ATC GAC CTC GCC CTG CGC GAG CTG CGC TAT
Tyr Glu Asn Ser Met Phe Ile Val Glu Gly Ile Asp Leu Ala Leu Arg Glu Leu Arg Tyr 450                                             480
GCC GGC ATC CAG GAC TTC AAA GTG GTG GTG CTC TCC TAC TGG GAC TTC GTC AAG GAC CCG
Ala Gly Ile Gln Asp Phe Lys Val Val Val Leu Ser Tyr Trp Asp Phe Val Lys Asp Pro 510                                             540
GCT GTG ATC CAG CAG CTC TAT CCC GAG GGC TTC CTC GGC TGG GAC ATC GAG CAC GGC GGC
Ala Val Ile Gln Gln Leu Tyr Pro Glu Gly Phe Leu Gly Trp Asp Ile Glu His Gly Gly 570                                             600
GTC TCC GAG ACC TCC CTG ATG CTG GCT TTG TAC CCG GAC CTG GTG GAC CTG GAC CGC GTC
Val Phe Glu Thr Ser Leu Met Leu Ala Leu Tyr Pro Asp Leu Val Asp Leu Asp Arg Val 630                                             660
GTC GAT CAC CCA CCT GCA ACC TTC CCA CCC TAT GAC GTG TTT CCG GTC GAC CCG GCC CGT
Val Asp His Pro Pro Ala Thr Phe Pro Pro Tyr Asp Val Phe Pro Val Asp Pro Ala Arg 690                                             720
ACG CCG GCG CCG GGC ACT CTG TCG TCG GCG AAG ACG GCC AGC CGA GAG AAG GGC GAG TTG
Thr Pro Ala Pro Gly Thr Leu Ser Ser Ala Lys Thr Ala Ser Arg Glu Lys Gly Glu Leu 750                                             780
ATC CTG GAG GTC TGC GTC CAG GGC ATT GCC GAC GCT ATC CGC GAG GAG TTC CCG CCC ACC
Ile Leu Glu Val Cys Val Gln Gly Ile Ala Asp Ala Ile Arg Glu Glu Phe Pro Pro Thr

TGA
```

DNA FRAGMENT CONTAINING A GENE ENCODING CREATININE AMIDOHYDROLASE

This is a continuation of application Ser. No. 07/538,274 filed on Jun. 14, 1990, now abandoned.

BACKGROUND OF THE INVENTION

1. Field of the Invention

The present invention relates to a DNA fragment that contains a gene encoding creatinine amidohydrolase, a recombinant vector containing the said DNA fragment and a transformant containing the said vector. Furthermore, the present invention also relates to a method for producing creatinine amidohydrolase by the use of the said transformant.

2. Description of the Prior Art

Creatinine amidohydrolase (EC 3.5.2.10) is an enzyme that catalyzes the following conversion reaction between creatinine and creatine.

Creatinine amidohydrolase is employed for the measurement of creatinine or creatine in blood serum or urine.

Creatinine amidohydrolase has been produced by cultivating microorganisms with the ability of producing creatinine amidohydrolase, such as Pseudomonas spp., in the presence of creatinine, creatine or a mixture of these two substances, and recovering creatinine amidohydrolase from the culture broth (Amino Acid• Nucleic Acid, Vol. 35, 39–46, 1977).

However, this method necessitates the addition of costly substances such as creatinine or creatine to the culture medium. Moreover, the yields of creatinine amidohydrolase obtained by this method have not been adequate. Therefore, the development of an efficient method for the production of creatinine amidohydrolase without the use of creatinine or creatine is desirable.

SUMMARY OF THE INVENTION

A DNA fragment of this invention contains a gene encoding creatinine amidohydrolase.

In a preferred embodiment, the said gene is derived from a microorganism belonging to the genus Pseudomonas.

Figure 1:
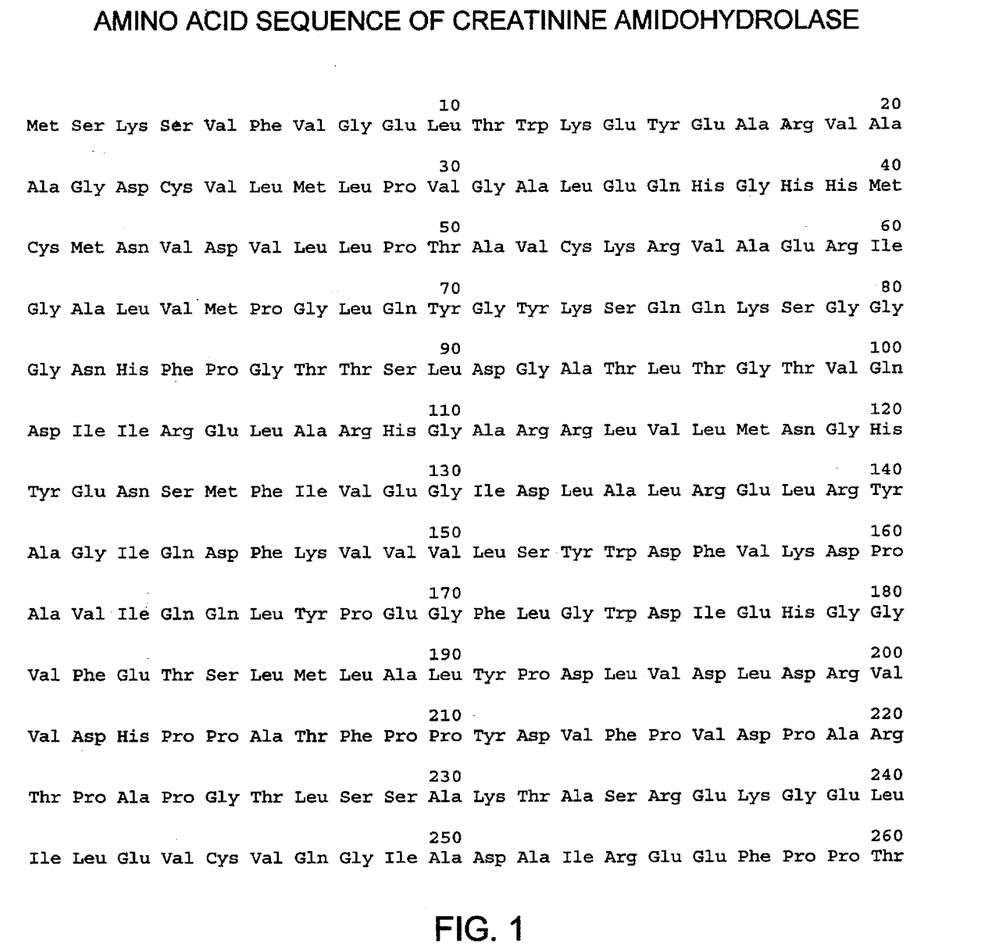
FIG. 1 shows the amino acid sequence that corresponds to the DNA sequence of the gene encoding creatinine amidohydrolase derived from Pseudomonas putida PS-7.

In a preferred embodiment, the said DNA sequence encodes the amino acid sequence of FIG. 1.

Figure 2:
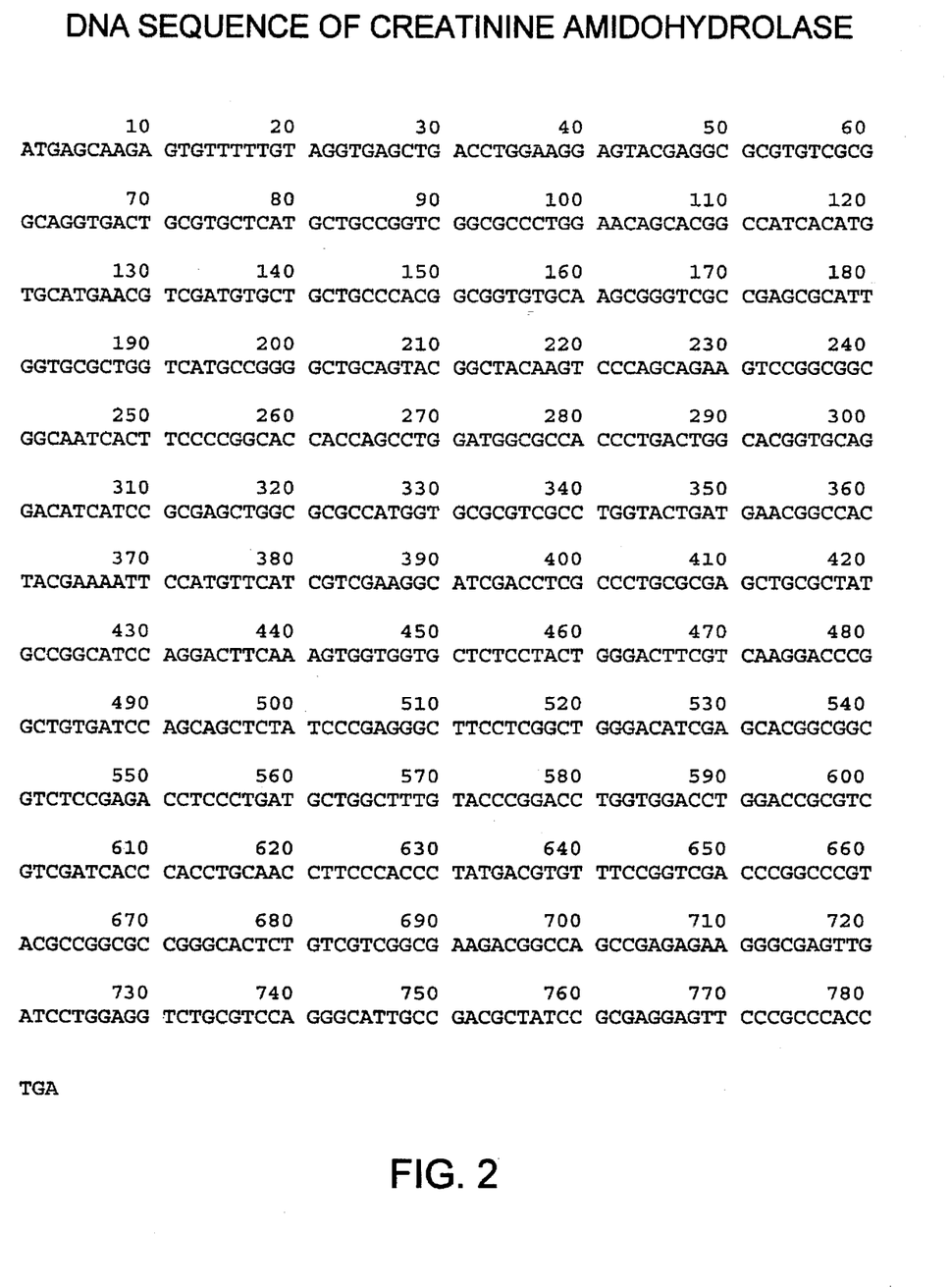
FIG. 2 shows the DNA sequence of the gene encoding creatinine amidohydrolase derived from Pseudomonas putida PS-7.

In a preferred embodiment, the DNA fragment contains a DNA sequence of FIG. 2.

A recombinant vector of this invention contains the above-mentioned DNA fragment.

A transformant of this invention carries the above-mentioned recombinant vector.

A method for producing creatinine amidohydrolase of this invention comprises: cultivating the above-mentioned transformant in a nutrient medium, and recovering creatinine amidohydrolase produced by the said transformant from the culture.

Thus, the invention described herein makes possible the objectives of: (1) providing a DNA fragment that contains a gene encoding creatinine amidohydrolase, (2) providing a recombinant vector having the aforementioned DNA fragment and capable of efficiently expressing the information contained in the said DNA fragment in a suitable host cell, (3) providing a transformant into which the said recombinant vector has been introduced, and (4) providing a method of producing creatinine amidohydrolase efficiently and economically by the use of the aforementioned transformant, without the addition of expensive substances such as creatinine or creatine to the culture medium.

BRIEF DESCRIPTION OF THE DRAWINGS

This invention may be better understood and its numerous objects and advantages will become apparent to those skilled in the art by reference to the accompanying drawings as follows:

FIG. 3 shows the DNA sequence of the gene encoding creatinine amidohydrolase derived from Pseudomonas putida PS-7, and the corresponding amino acid sequence.

DESCRIPTION OF THE PREFERRED EMBODIMENTS

In order to solve the problems of the prior arts, the present inventors have studied a method for producing creatinine amidohydrolase by utilizing a DNA fragment that contains a gene encoding creatinine amidohydrolase, a recombinant vector containing the said DNA sequence and a transformant containing the said vector. As a result of these studies, the present inventors succeeded in cloning a creatinine amidohydrolase gene possessed by an organism which produces creatinine amidohydrolase, isolating a DNA fragment containing the said gene, and determining the DNA sequence of the said gene. Next, the inventors constructed a recombinant vector having the said DNA fragment, obtained a transformant containing the said vector, and succeeded in producing creatinine amidohydrolase by using the said transformant, thereby completing the present invention.

The individual steps involved in the implementation of the present invention will hereafter be described in detail.

(A) Preparation of a DNA fragment that contains a gene encoding creatinine amidohydrolase, and recombinant vector containing the same DNA fragments that contain a gene encoding creatinine amidohydrolase are prepared from a microorganism capable of producing creatinine amidohydrolase. The recombinant vector of the present invention can be obtained by introducing this DNA fragment into a suitable vector DNA which is capable of replication within the cells of the cultivated host microorganism, for example, Escherichia spp., etc.

The aforementioned gene encoding creatinine amidohydrolase can be obtained, for example, from *Pseudomonas putida* PS-7 by the following procedure. For example, a culture broth is obtained by cultivating this strain in a suitable medium. This culture broth is, for example, centrifuged at 5,000 rpm or higher, preferably at 8,000–10,000 rpm, for a period of 5 minutes or more, preferably 10–15 minutes, thereby obtaining pelleted cell bodies of *Pseudomonas putida* PS-7.

Chromosomal DNA can be obtained from these cell bodies by, for example, the methods described in "Recombinant DNA Techniques" (Rodriguez R. L. et al., Addison-Wesley Publishing Company, 1983), or by the method of Koizumi J. et al. (Biotech. Bioeng., 27, 721–728, 1985), etc.

This chromosomal DNA is cleaved by allowing a suitable restriction enzyme, for example, 1–100 units of EcoRI (Toyobo Co., Ltd.), to act upon the DNA at a temperature of 30° C. or more, preferably at 37° C., for a period of at least 30 minutes, preferably 1–2 hours, thereby obtaining a mixture containing chromosomal DNA fragments of various sizes.

DNA fragments of low molecular weight (less than 1 kb) are then removed from the mixture of DNA fragments obtained in this manner by, for example, sucrose gradient centrifugation, and then fragments larger than 1 Kb are concentrated by methods such as ethanol precipitation, thereby obtaining a mixture of DNA fragments larger than 1 Kb containing a gene encoding creatinine amidohydrolase.

Various types of vector DNA can be used for the purpose of the present invention, for example, plasmid vector DNA, bacteriophage vector DNA, etc., can be used. Particularly suitable examples are the plasmid vectors pBR322 or pUC19 (Toyobo Co., Ltd.), the bacteriophage vectors λZAP or EMBL3 (Stratagene), and similar vectors.

Next, the above-mentioned mixed DNA fragments that contain the gene encoding creatinine amidohydrolase are subjected to ligation reaction with the aforementioned vector DNA. This ligation can be performed using, for example, *E. coli* DNA ligase, or T4-DNA ligase. Preferably, 1–100 units of T4-DNA ligase is allowed to react at 4°–37° C., preferably 4°–16° C., for a period of at least one hour, preferably 4–16 hours, thereby obtaining recombinant vectors containing various DNA fragments.

An appropriate host cell, for example, *E. coli* K-12, preferably *E. coli* JM109, *E. coli* HB101, or *E. coli* XL1-blue (Stratagene), etc., is then transformed or transduced with these recombinant vectors, thereby obtaining a pool of transformants. This transformation or transduction can be accomplished, for example, by the methods described in "Molecular Cloning" (Maniatis, T., et al., Cold Spring Harbor, 1982).

The transformants are screened for the ability to produce creatinine amidohydrolase, and the recombinant vectors possessed by the positive transformants are obtained. The recombinant vectors are cleaved into small fragments by the conventional techniques, and obtained small DNA fragment encoding creatinine amidohydrolase is ligated with a suitable plasmid vector (i.e., a vector for expression), resulting in a recombinant plasmid that contains a gene encoding creatinine amidohydrolase. By using appropriate restriction enzymes, the DNA fragment encoding creatinine amidohydrolase was cleaved out of a recombinant plasmid that had been obtained in this manner. The DNA sequence of the fragment was identified and found to be that shown in FIG. 2 or 3.

(B) Preparation of transformants

Using a suitable transformation method, the recombinant vector containing the DNA sequence that contains the gene encoding creatinine amidohydrolase, obtained in this manner, can be introduced into a microorganism belonging, for example, to the genus Escherichia, the genus Pseudomonas, or the genus Bacillus, etc. Thus, transformants possessing characteristics imparted by both the desired gene and the vector DNA are obtained.

Suitable strains of the aforementioned Escherichia spp. include *E. coli* JM109, *E. coli* HB101, *E. coli* C600, *E. coli* DH-1, etc. One specific example of a satisfactory transformant obtained in this manner was *E. coli* JM109 (pCNH521) (FERM BP-2930).

(C) Production of creatinine amidohydrolase

A culture medium suitable for the growth of the host microorganism and, moreover, suitable for the production of creatinine amidohydrolase is employed for the growth of the transformant.

For example, media ordinarily employed for the cultivation of Escherichia spp., such as LB medium (containing trypton, yeast extract and sodium chloride), BPB medium (containing polypeptone, yeast extract and potassium phosphate; Difco), nutrient agar medium (Difco 0001) or trypton-sodium chloride medium can be used as basic culture media for the present purpose. In addition, if necessary, carbon sources, nitrogen sources, and nutrients such as amino acids and vitamins can be added.

The transformants can ordinarily be cultivated by shaking or stirring cultures. The cultivation temperature should be regulated so as to remain in the range of 20°–45° C., preferably in the vicinity of 37° C., and the pH should be in the range of 5–8, preferably in the vicinity of 7. However, other conditions are also permissible, merely provided that the bacterial strain used can grow under these conditions. Cultivation of the transformant for one to two days will result in production of creatinine amidohydrolase and accumulation of this substance within the cell bodies.

Recovery and purification of the creatinine amidohydrolase so produced can be accomplished by conventional methods. For example, the cells are demolished by ultrasonication, mechanical disintegration with glass beads, a French press, or the action of surfactants, etc., and a crude extract is obtained. This crude extract can be purified by various well-known methods such as salting out with ammonium sulphate or Glauber's salt, metallic coagulation with salts such as magnesium chloride or calcium chloride, coagulation with agents such as protamine or polyethylene imine, ion exchange chromatography with DEAE (diethylaminoethyl)-sepharose (Pharmacia) or CM (carboxymethyl)-cellulose (Pharmacia), etc., and gel filtration with Sephacryl S-300 (Pharmacia), etc., thereby obtaining a purified creatinine amidohydrolase.

The physicochemical properties of the purified creatinine amidohydrolase obtained by the aforementioned purification procedures were entirely identical with those of the creatinine amidohydrolase produced by the DNA donor strain, e.g., *Pseudomonas putida* PS-7.

As is well known, the DNA sequence encoding a given amino acid sequence is not uniquely determined, and a number of DNA sequences are possible. Therefore, the present invention includes not only the DNA sequence shown in FIGS. 2 and 3, but also all other DNA sequences encoding the amino acid sequence of creatinine amidohydrolase shown in FIGS. 1 and 3. Generally, using recombinant DNA techniques, artificial mutations can be induced at specific sites on a basic DNA sequence in such a manner that the essential properties of the polypeptide encoded by the said DNA are either unaltered or improved. Thus, the aforementioned DNA sequence encoding the amino acid sequence of creatinine amidohydrolase can also be converted to a modified sequence which encodes creatinine amidohydrolase with properties equivalent or superior to those of natural creatinine amidohydrolase by artificial insertions, deletions or substitutions. Of course, the DNA sequences of the present invention also include such modified DNA sequences.

EXAMPLES

The present invention will be explained in more detail with reference to the following examples.

(1) Preparation of chromosomal DNA derived from *Pseudomonas putida* PS-7.

Cells of *Pseudomonas putida* PS-7 were inoculated into 100 ml of nutrient medium containing 2.0% polypeptone, 0.4% yeast extract, 0.1% malt extract, 0.3% potassium dihydrogen phosphate, 1.4% dipotassium hydrogen phosphate, 0.01% magnesium sulphate and 2.0% glucose. The mixture was shake cultured at 30° C. for 8 hours. This culture was centrifuged at 12,000 rpm for 10 minutes, thereby obtaining approximately 1 g of wet pelleted cells. Next, approximately 1.8 mg of chromosomal DNA was isolated from the cells by the method described in "Recombinant DNA Techniques" (Rodriguez R. L. et al., Addison-Wesley Publishing Company, 1983). Next, 100 µg of this chromosomal DNA was digested with 50 units of the restriction enzyme EcoRI (Toyoho Co., Ltd.) at 37° C. for 3 hours. After digestion, the reaction mixture was subjected to 5–20% sucrose gradient centrifugation, thereby obtaining approximately 10 µg of DNA fragments in the 1–10 kb fraction.

(2) Preparation of DNA fragment that contains a gene encoding creatinine amidohydrolase and recombinant vector containing the said DNA fragment First, 1 µg of the bacteriophage vector λZAP (EcoRI-cleaved, Stratagene) and 0.5 µg of the EcoRI-cleaved chromosomal DNA obtained in section 1 were allowed to react at 16° C. for 12 hours in the presence of 1 unit of T4-DNA ligase (Toyobo Co., Ltd.) to effect ligation of the two varieties of DNA fragments. This ligated DNA was then packaged with a λDNA in vitro packaging kit (Gigapack Gold, Stratagene). Then, using the method described in "Molecular Cloning" (Maniatis, T., et al. Cold Spring Harbor, 1982), the recombinant phage obtained by this packaging operation was transduced into *E. coli* XL1-blue (Stratagene; Nucleic Acid Research Vol. 16, No. 15, 7583–7600, 1988). Approximately $1\times10^6$ phage plaques were obtained per one microgram of the phage vector DNA.

The recombinant phage that contains a DNA fragment having the gene encoding creatinine amidohydrolase was selected by an enzyme immunoassay, using a Gene Expression Kit (Boehringer Mannheim). The limit of detection of creatinine amidohydrolase by this enzyme immunoassay is approximately 100 pg, and approximately 1–2 positive signals per 1000 phage plaques were detected using the test kit.

Recombinant plasmids were obtained from these three plaques which reacted positively in the enzyme immunoassay in accordance with the instructions in the user's manual for the Stratagene λZAP phage vector. The three varieties of recombinant plasmids so obtained were cleaved with EcoRI, and a 4.2 kb DNA fragment common to all three varieties was detected. Approximately 2 µg of this EcoRI-cleaved fragment was then further cleaved with ApaI (Toyobo Co., Ltd.). The resulting DNA fragments were separated according to size in a low melting point agarose gel, and a 2.5 kb ApaI-EcoRI fragment was isolated.

The isolation of this DNA fragment from the low melting point agarose gel was performed in accordance with the method of K. Struhl (Biotechniques, 3,452, 1985). All other isolations of DNA fragments were also performed by this method.

Figure 4:
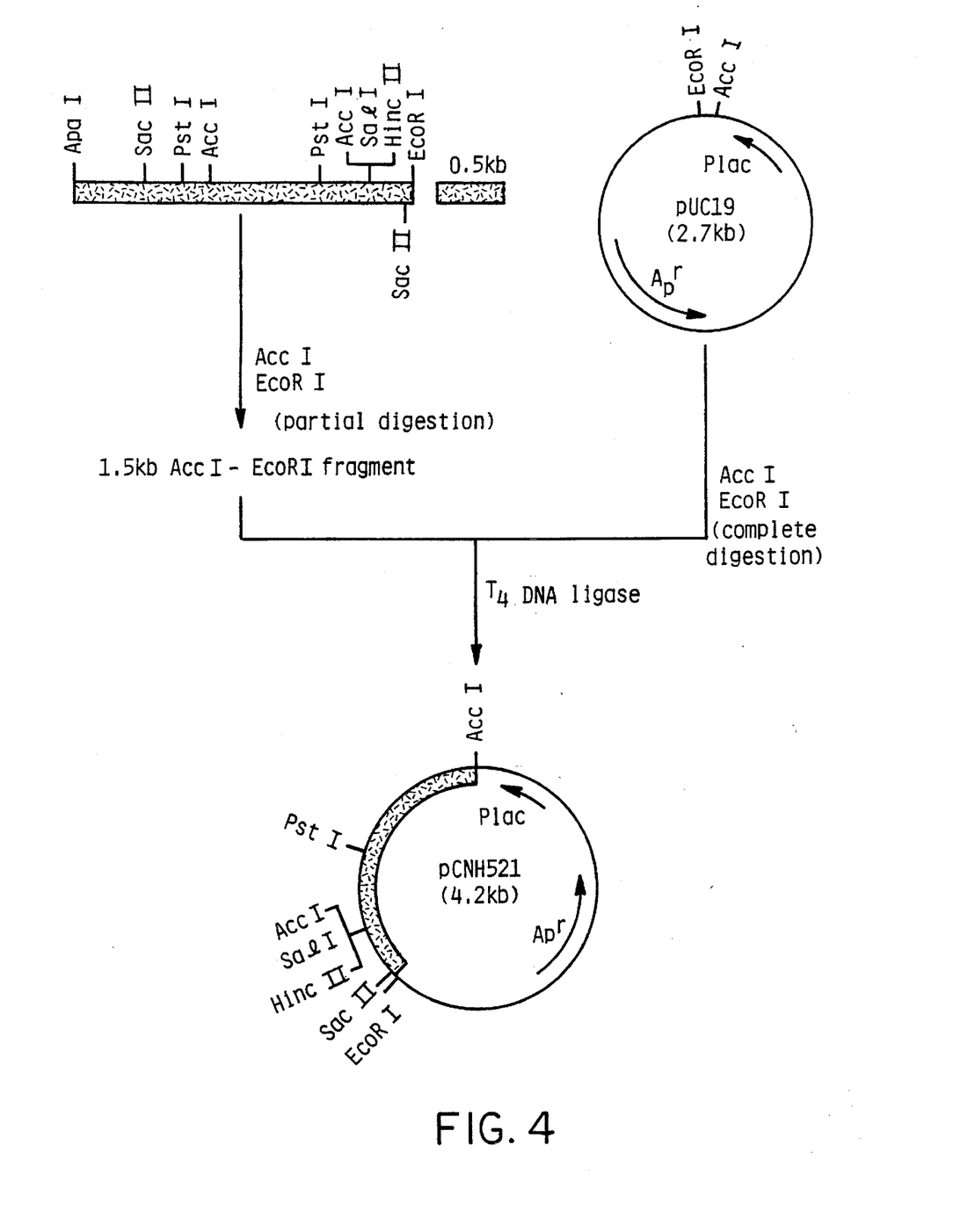
FIG. 4 is a schematic diagram illustrating the construction of the recombinant vector pCNH521 of the present invention from a 1.5 kb DNA fragment derived from Pseudomonas putida PS-7 and the plasmid pUC19.

Approximately 1 µg of the plasmid vector Bluescript KS (M13-) (Stratagene) was cleaved with ApaI and EcoRI. This digested plasmid vector was mixed with approximately 0.5 µg of the 2.5 kb ApaI-EcoRI fragment prepared in the manner described above, and these two varieties of DNA fragments were then ligated by a reaction that was carried out at 16° C. for 12 hours, in the presence of 1 unit of T4-DNA ligase, thereby obtaining a recombinant plasmid pCNH2. The said 2.5 kb ApaI-EcoRI fragment has various restriction sites as shown in FIG. 4.

Next, approximately 2 µg of the aforementioned 2.5 kb ApaI-EcoRI fragment was partially digested by a 1 hour reaction at 37° C. in the presence of 0.5 unit of AccI (Toyobo Co., Ltd.), and a 1.5 kb AccI-EcoRI fragment was isolated in accordance with the aforementioned method of K. Struhl. Also, approximately 1 µg of the plasmid pUC19 (Toyobo Co., Ltd.) was digested with AccI and EcoRI, then this digested plasmid was mixed with approximately 0.5 µg of the 1.5 kb AccI-EcoRI fragment prepared in the manner described above. The mixture was allowed to react at 16° C. for 12 hours in the presence of 1 unit of T4-DNA ligase, thereby ligating the two varieties of fragments and obtaining the recombinant plasmid pCNH521 (see FIG. 4). In the cell of *E. coli*, this plasmid pCNH521 efficiently produced biologically active creatinine amidohydrolase under the control of the lac promoter.

On the other hand, the said 1.5 kb AccI-EcoRI fragment was digested with various restriction enzymes and ligated with M13mp18 or M13mp19 phage DNA (Toyobo Co., Ltd.), after which single-stranded DNA was prepared from this ligated material by the usual method. The DNA sequence of the single-stranded DNA so obtained was determined with an M13 Sequencing Kit (Toyobo Co., Ltd.). The DNA sequence determined in this manner and the corresponding amino acid sequence are shown in FIG. 3.

(3) Preparation of transformants carrying plasmids with DNA encoding creatinine amidohydrolase Using the aforementioned recombinant plasmid pCNH521, which contains a DNA fragment having a gene encoding creatinine amidohydrolase, cells of the *E. coli* JM109 (Toyobo Co., Ltd.; Gene, Vol. 33, 103–119, 1985) were transformed in accordance with the method described in "Molecular Cloning" (Maniatis, T., et al., Cold Spring Harbor, 1982), thereby obtaining a transformant *E. coli* JM109 (pCNH521). *E. coli* JM109 (pCNH521) has been deposited with the Fermentation Research Institute under Accession No. FERM BP-2930 transferred from FERM P-10748, where it will be maintained under the terms of the Budapest Treaty. This transformant efficiently produced creatinine amidohydrolase in the presence of IPTG (isopropyl-β-D-thiogalactopyranoside; Nakarai-Tesque), a lac promoter inducer. The maximum yield of creatinine amidohydrolase was approximately 40% of the intracellular soluble protein constituents.

The production of creatinine amidohydrolase by the transformants of the present invention as well as the aforementioned *Pseudomonas putida* PS-7 strain were evaluated, and the results are shown in Table 1. The strain *E. coli* JM109 (pCNH2) shown in Table 1 is the transformant obtained by transforming *E. coli* JM109 with the recombinant plasmid pCNH2 containing the 2.5 kb ApaI-EcoRI fragment obtained as indicated in the previous section 2.

The activity of creatinine amidohydrolase was measured as follows. First, 0.1 ml of the enzyme solution was added to 0.9 ml of 0.1M creatine solution. After allowing the enzymatic reaction to proceed for 10 minutes at 37° C., the amount of creatinine produced was assayed by the Jaffe reaction (Clin. Chem., 1, 55, 1953). The enzyme activity of creatinine amidohydrolase that produces 1 μmol of creatinine per minute is taken to be one unit.

*Pseudomonas putida* PS-7 was cultivated in accordance with the method described in Amino Acid• Nucleic Acid Vol. 35, 37–46, 1977. The above-mentioned *E. coli* strains were cultivated in LB medium (containing 1% trypton, 0.5% yeast extract, 1% sodium chloride, 50 μg/ml ampicillin, pH 7.4) respectively, with or without the addition of 0.2 mM of IPTG, at a temperature of 37° C. for 16 hours. Intracellular enzymatic activity in these bacteria was also measured.

TABLE 1

| Microorganism | Activity (U/ml) | Additive |
| --- | --- | --- |
| *Pseudomonas putida* PS-7 | 0 | Creatinine− |
| *Pseudomonas putida* PS-7 | 1.8 | Creatinine+ |
| *E. coli* JM109 (pCNH2) | 1.3 | −IPTG |
| *E. coli* JM109 (pCNH2) | 6.9 | +IPTG |
| *E. coli* JM109 (pCNH521) | 3.3 | −IPTG |
| *E. coli* JM109 (pCNH521) | 17.1 | +IPTG |

The above data indicates that creatinine amidohydrolase was produced with high efficiency in *E. coli* JM109 (pCNH521) under the control of the lac promoter without the induction by creatinine.

(4) Production of creatinine amidohydrolase and purification of the enzyme

First, 6-liter portions of the aforementioned LB medium (containing 1% trypton, 0.5% yeast extract, 1% sodium chloride, pH 7.4) were loaded into 10-liter jar fermenters, which were then autoclaved at 121° C. for 15 minutes. After the jars had been left to cool, 6 ml of a 50 mg/ml solution of ampicillin (Nakarai Tesque) as well as 6 ml of a 200 mM solution of IPTG were aseptically added to each jar. This medium was inoculated with 60 ml (per jar) of a culture broth of *E. coli* JM109 (pCNH521) which had been prepared beforehand by shake culturing for 16 hours at 37° C. in a medium of the same composition as mentioned above. The inoculated medium was then incubated at 37° C. for 16 hours with aeration and stirring. After incubation was completed, the activity of creatinine amidohydrolase in the broth was 15.7 U/ml. Then, 6 liters of this culture broth was centrifuged to pellet the bacterial cells, which were then resuspended in 200 ml of 50 mM potassium phosphate buffer solution (pH 7.5) and ultrasonicated by the usual method. The mixture after ultrasonication was centrifuged at 15,000 rpm, thereby obtaining a crude enzyme solution of creatinine amidohydrolase.

The crude enzyme solution obtained in this manner was then treated with polyethylene imine to remove nucleic acid, then fractionated by salting-out with ammonium sulphate. The salted-out precipitates were dissolved in 50 ml of 50 mM potassium phosphate buffer solution (pH 7.5), and this solution was subjected to column chromatography using DEAE-Sepharose (Pharmacia) which had been equilibrated with a 50 mM potassium phosphate buffer solution, pH 7.5. Elution with 0–0.5M sodium chloride gradient was performed, and the active creatinine amidohydrolase fraction was eluted in the sodium chloride concentration range of 0.1–0.3M. This active creatinine amidohydrolase fraction was concentrated by ultrafiltration, and then subjected to gel filtration through Sephadex G-25 (Pharmacia) which had been equilibrated with a 50 mM potassium phosphate buffer solution, pH 7.5. Finally, 49000 units of purified creatinine amidohydrolase powder were obtained by lyophilization in accordance with the usual technique. The yield was 52%.

Figure 5:
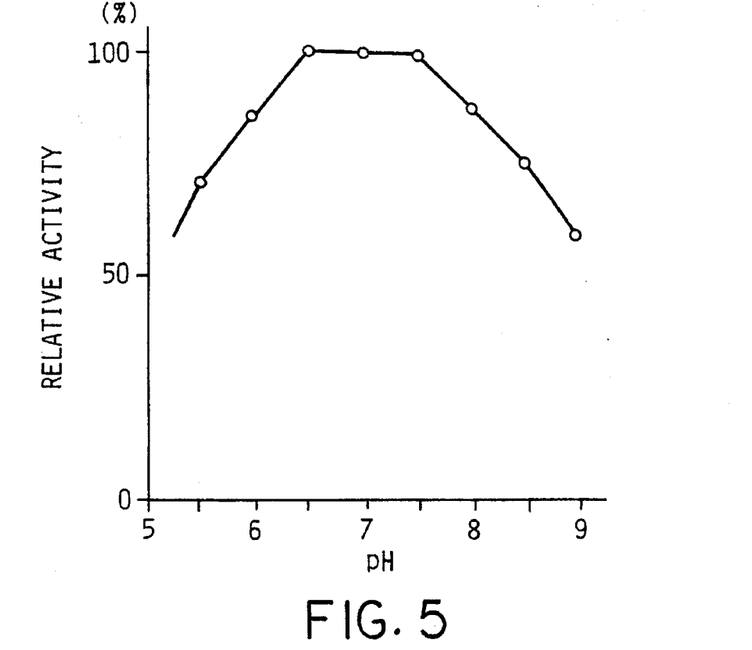
FIG. 5 is a graph showing the optimal pH of the creatinine amidohydrolase obtained by the method of the present invention.
Figure 6:
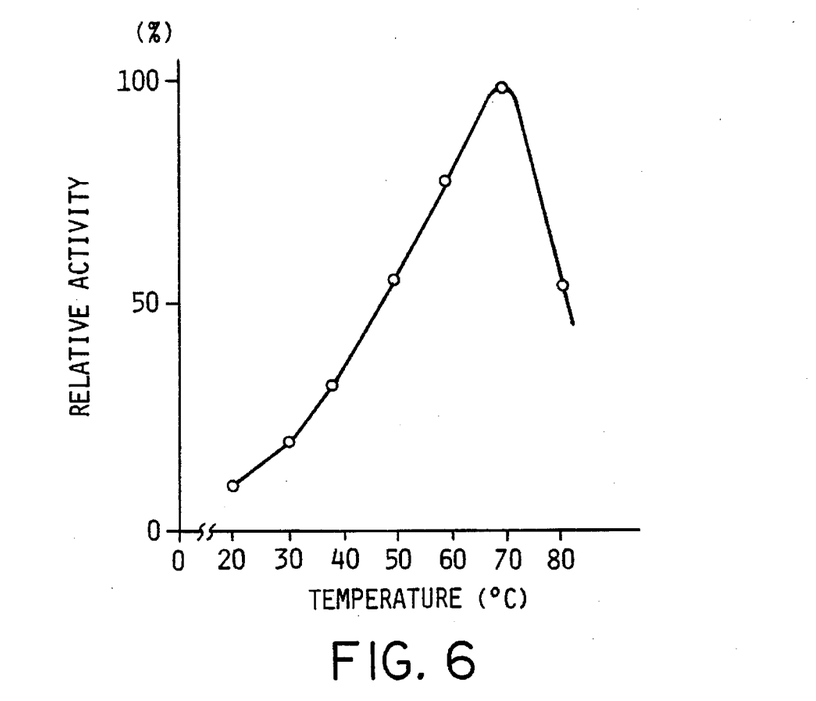
FIG. 6 is a graph showing the optimal temperature of the creatinine amidohydrolase obtained by the method of the present invention.
Figure 7:
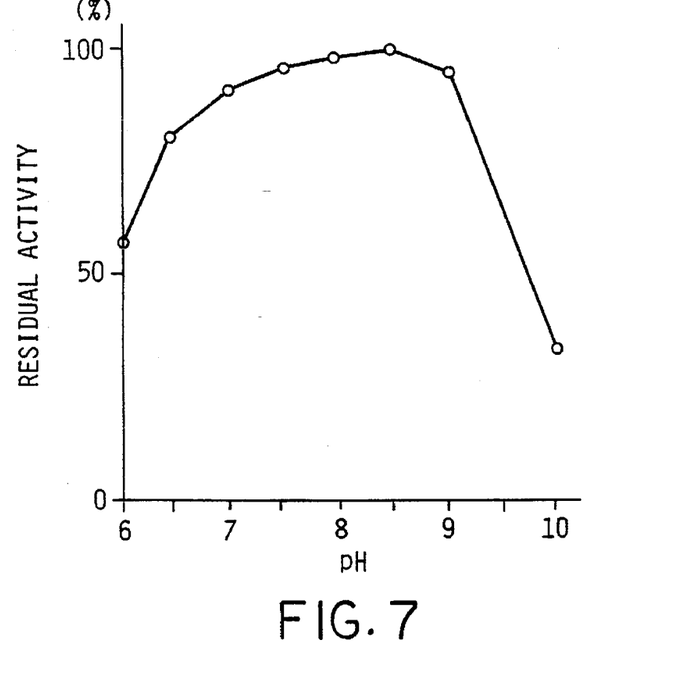
FIG. 7 is a graph showing the pH stability of the creatinine amidohydrolase obtained by the method of the present invention.
Figure 8:
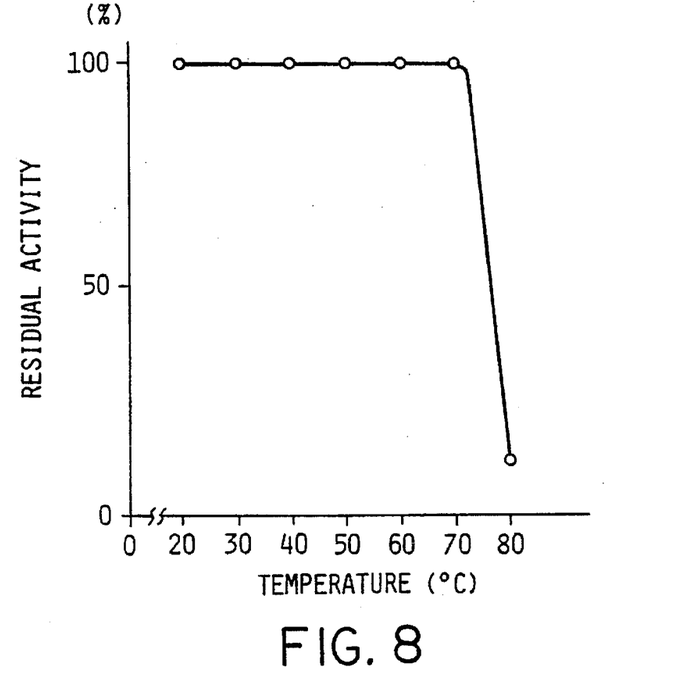
FIG. 8 is a graph showing the thermal stability of the creatinine amidohydrolase obtained by the method of the present invention.

The properties of the enzyme so obtained were investigated. The optimum pH and the thermal stability of this enzyme are shown in FIGS. 5 and 6, respectively. The buffer solutions used as media for the reactions when enzyme activity was assayed were a 50 mM acetate buffer at pH 5.5, a 50 mM potassium phosphate buffer in the pH range of 6.0–8.0 and a 50 mM carbonate buffer in the pH range of 8.5–9.0. The pH and thermal stability of this enzyme are shown in FIGS. 7 and 8, respectively. In the tests for the evaluation of pH stability, the enzyme was maintained at a temperature of 5° C. for a period of 16 hours in a 50 mM potassium phosphate buffer solution at pH 6.0–8.0 and in a 50 mM carbonate buffer solution at pH 8.5–9.0. The physicochemical properties of this creatinine amidohydrolase obtained were substantially identical with those of the creatinine amidohydrolase produced by the DNA donor strain, e.g., the *Pseudomonas putida* PS-7.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. An isolated DNA sequence comprising a DNA sequence encoding creatinine amidohydrolase, wherein said creatinine amidohydrolase has an amino acid sequence of FIG. 1.

2. The DNA sequence according to claim 1, which is a DNA sequence of FIG. 2.

3. A recombinant vector comprising the DNA sequence of claim 1 in operable linkage with a transcriptional promoter.

4. A transformant that carries the recombinant vector of claim 3.

5. A method for producing creatinine amidohydrolase comprising:

cultivating the transformant of claim 4 in a nutrient medium, and recovering creatinine amidohydrolase from a lysate of the cultured transformants.

* * * * *